(12) United States Patent
Sangwan et al.

(10) Patent No.: US 7,108,870 B2
(45) Date of Patent: Sep. 19, 2006

(54) PROCESS FOR ISOLATION OF WITHAFERIN-A FROM PLANT MATERIALS AND PRODUCTS THEREFROM

(75) Inventors: Rajender Singh Sangwan, Lucknow (IN); Narayan Das Chaurasiya, Lucknow (IN); Laxmi Narayan Misra, Lucknow (IN); Payare Lal, Lucknow (IN); Girish Chandra Uniyal, Lucknow (IN); Neelam Singh Sangwan, Lucknow (IN); Avdhesh Kumar Srivastava, Lucknow (IN); Krishan Avtar Suri, Jammu (IN); Ghulam Nabi Qazi, Jammu (IN); Rakesh Tuli, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 99 days.

(21) Appl. No.: 10/822,858

(22) Filed: Apr. 13, 2004

(65) Prior Publication Data
US 2005/0226950 A1    Oct. 13, 2005

(51) Int. Cl.
*A61K 36/00* (2006.01)
*A61K 31/35* (2006.01)
(52) U.S. Cl. .................... 424/725; 514/453
(58) Field of Classification Search ............. None
See application file for complete search history.

(56) References Cited

U.S. PATENT DOCUMENTS

| | | | | |
|---|---|---|---|---|
| 5,494,668 A | * | 2/1996 | Patwardhan | 424/756 |
| 6,153,198 A | * | 11/2000 | Ghosal | 424/773 |
| 6,713,092 B1 | * | 3/2004 | Ghosal | 424/725 |
| 6,866,872 B1 | * | 3/2005 | Tomi et al. | 424/725 |
| 2004/0033273 A1 | * | 2/2004 | Patwardhan et al. | 424/725 |
| 2004/0096524 A1 | * | 5/2004 | Nair et al. | 424/725 |
| 2004/0258781 A1 | * | 12/2004 | Nair et al. | 424/769 |

FOREIGN PATENT DOCUMENTS

JP    20020187846    * 7/2002

OTHER PUBLICATIONS

Dinan et al. J. Chromatogr. A. 2001. vol. 935, pp. 105-123.*
Kaufmann et al. Chromatographia. 2001. vol. 54, pp. 394-398.*

* cited by examiner

Primary Examiner—Christopher R. Tate
(74) Attorney, Agent, or Firm—Buchanan Ingersoll & Rooney, PC

(57) ABSTRACT

The present invention relates to an improved process of analytical and quantitative isolation of withaferin-A from *Withania somnifera* (Sanskrit: Ashwagandha, English: winter cherry) and other plants and products therefrom, said method comprising steps of selecting most appropriate extraction medium composition, with extraction solvent system consisting of a defined admixture of water and alcohol in a range of proportion of alcohol within a narrow range of (methanol, ethanol etc.) (preferably 60% alcohol and 40% water) for the dry plant material and from 60% to 80% alcohol in the alcohol-water mixture for fresh plant material, the invented extractant composition leading to better/improved yields and accurate quantitative estimations of withaferin A existent in planta or in materia, selecting effective state of the tissue particularly use of the fresh materials improving yields, providing logistic benefits of isolations and diagnosis, and according several other advantages including technological, economic, preventing contaminations etc., the said method being valuable and advantageous for standardization of botanicals, metabolomic characterization of plants particularly chemotypes, analyzing metabolic transitions under physiological, genetical, environmental and biotic perturbations.

14 Claims, 1 Drawing Sheet

Figure 1:
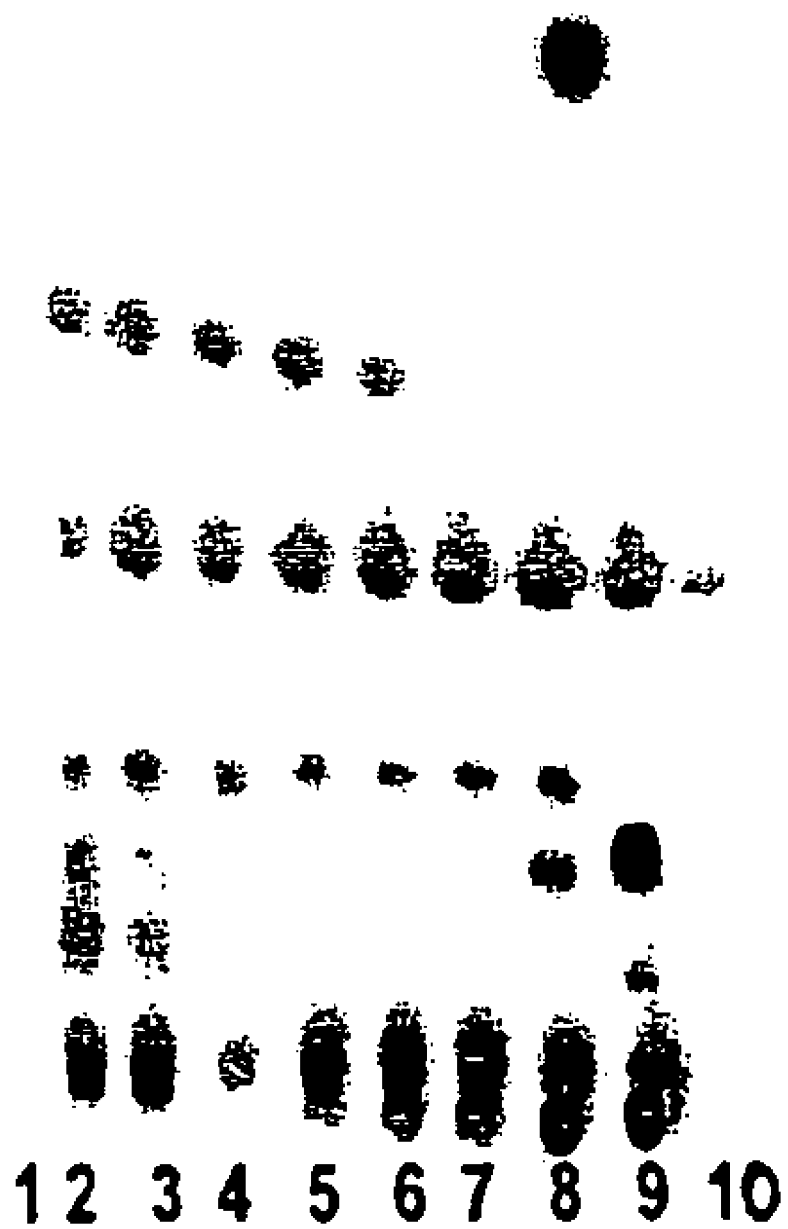

PROCESS FOR ISOLATION OF WITHAFERIN-A FROM PLANT MATERIALS AND PRODUCTS THEREFROM

FIELD OF THE INVENTION

The present invention relates to an improved process for analytical and quantitative isolation of withaferin-A from plant materials and products therefrom, said method comprising steps of selecting effective extractant solvent system, with extraction solvent system consisting of a defined admixture of water and alcohol in a range of proportion of alcohol (methanol, ethanol or other alcohol) with comparable nature of polarity, dielectic constant and dipole moment etc.) from 60 to 70% (preferably 60%) for dry material and from 60 to 80% (preferably 60%) for fresh material, with the fresh material process providing improved recovery and more accurate estimations, process with aqueous extraction of withaferin-A and augmentation of recovery of withaferin-A from such aqueous extraction residues also forms the part of the invented process, with processes and methods involving different extractant system leading for ways and means of improvement of withaferin-A recovery and its accurate estimation etc. from different states of biomass and products therefrom, better yields and quantitative estimations of withaferin-A existent in planta or in material in conjunction with state of the tissue specific extraction systems including use of the fresh materials for improving yields/estimations providing logistic benefits of isolations and diagnosis, and according several other advantages including technological, economic, preventing contaminations etc., the said method being valuable and advantageous for, metabolomic characterization of plants particularly chemotypes, analyzing metabolic transitions under physiological, genetical, environmental and biotic perturbations in the plant and materials of *Withania* and other congener species and for standardization of botanicals, products and formulations therefrom for better label claims and accurate rating. Thus, the essence of field of invention is development of a process for efficient isolation and accurate quantitative estimation of withaferin-A (a withanolide or withasteroid) in cells, plants, tissues and products, preparations and formulations therefrom using metabolomic techniques comprising precise extraction conditions and state of the tissues, liquid-liquid partitioning, flash-evaporation, sample preparation and analytical high performance liquid chromatographic resolution and quantification in said method to determine quantitative, qualitative, native composition of materials and products therefrom.

BACKGROUND AND PRIOR ART REFERENCE

Ashwagandha is one of the most valuable medicinal plants, forming the active component or whole of the phytopharmaceutical products for the prevention and cure of a variety of human ailments and diseases. Numerically, Ayurvedic, Unani and Sidha medicinal products based on the plant currently run above one hundred and it is rapidly expanding worldwide. The plants, plant parts, crude extracts and other phytomatrices/preparations of ashwagandha are often sold on the basis of withaferin-A, besides the preponderance of withanolides on the whole. Increasing evidences suggest that different withanolides are associated with different levels of pharmaco-efficiencies directed towards different ailments. Withaferin-A is one of the most pharmacologically active constituents. The emerging global trends in herbal products not only emphasize on better-descript and specific lable claims but also assert stringencies of compliances of regulatory frameworks like compliances like DSHEA, NHPR and other analogous regulatory acts and statutes. To cater to these and other needs, Therefore, appropriateness of the methodolocal processes for extractions described herein is not only of tremendous importance for the better and improved yields, resource characterization and accurate quantitative estimations existent in planta or in material, but also provides benefits and logistics of isolations, diagnosis, metabolomics etc. The process is valuable and advantageous in global scale of applications and relevance for standardization of ashwgandha botanicals, metabolomic characterization of plants, chemotypes, analyzing the nature and pace of metabolic transitions under physiological, genetical, environmental and biotic perturbations etc.

Withanolides or withasteroids are a group of naturally occurring $C_{28}$-steroidal lactone molecules of basically triterpene ancestory and are structurally based on an intact or rearranged ergostane framework. The characteristic lactone is formed through conjoining of $C_{22}$ hydroxyl and $C_{26}$ carboxylic acid function. Thus, chemically withanolides are defined as 22-hydroxy ergostane-26-oic acid 26,22-lactone. Biogenesis of withasteroids is known to occur highly scarcely like *Tacca plantaginea* of Taccaceae (Z. L. Chen, B. D. Wang and J. H. Shen, 1988, Phytochemistry 29, 2999), *Cassia siamae* of Leguminoseae (C. Srivastava, I. R. Siddiqui, J. Singh and H. P. Tewari, 1992, J. Ind. Chem Soc. 69, 111), *Ajuga parviflora* of Labiatae (P. M. Khan, S. Ahmad, H. Rubnawaz and A. Malik, 1999, Phytochemistry, 51, 669; P. M. Khan, S. Ahmad and H. R. Nawaz, 1999, J. Nat. Prod. 62, 1290; H. R. Nawaz, A. Malik, P. M. Khan and S. Ahmad, 1999, Phytochemistry, 52, 1357) beyond their usual species limited prodigal producers i.e. 16 out of 96 genera of potato family (Solanaceae). These include, besides the well known Ayurvedic, Sidha, and Unani medicinal plant, Ashwagandha (winter cherry, *Withania somnifera*), *Lycium, Datura, Iochroma, Physalis, Tubocapsicum, Solanum* etc. Most of these plants are valued and/or used as: herbs or health foods and/or medicinal plants (based on the traditional knowledge of their positive support to body functions and responses), healing and healthful materials (as such or in the form of supplements, nutraceuticals, concoctions, formulations and compositions) althrough individual's age of growing and graying, rejuvenating and as remedial herbal products of acceptance, source of valuable phytoceuticals/phytochemicals with potentials of lead multifunction drugs/nutraceuticals of near future. Withaferin-A (ergostanically named as 4β, 27-dihydroxy-5β, 6β-epoxy-1-oxowitha-2,24-dienolide), the first member of this group of compounds was isolated from the well known Indian medicinal plant Ashwagandha (P. A. Kurup, 1956, Antibiotic principle of the leaves of *Withania somnifera*, Current Science, India, 25: 57) and its structure elucidated in 1965 (D. Lavie, E. Glotter and Y. Shvo, 1965, Constituents of *Withania sonmifera* Dun—the structure of withaferin A, J. Chem. Soc. 7517). Besides it is known to occur as one of the major withanolides in other *Withania* species (*W. aristica, W. coagulans, W. futescens*), *Acnistus arborescens, Iochroma coccinium, Physalis viscosa*. Withanolides are known to possess diverse biological and pharmacological activities. Particularly, withaferin-A, has several hard evidences, established through prolific studies of modern and state of the art research approaches of both in vivo and in vitro kind, of having valuable and a range of pharmacological activities including antibacterial (S. Chatterjee and S. K Chakraborty, 1980, Antimicrobial activity of some antineoplastic and other withanolides. Antonie van Leeuwenhoek 46, 59), cytotoxicity of KB cell cultures, inhibition of Sarcoma 180 and Walker intramuscular carcinosarcoma 256 tumors (S. M. Kupchan, W. K. Anderson, P. Bollinger, R. W. Doskotch, R. M. Smith, J. A. S. Renauld, R. H. K. Schnoes, A. L. Burlingame and D. R. Smith, 1969, Tumor inhibitors-active principles of *Acnistus arborescens*, Isolation and structural and spectral studies of withaferin-A and withacnistin, J. Org. Chem. 34: 3858), retardation of Ehrlich ascites carcinoma, arresting human larynx carcinoma cells at metaphase (B. Shohat, 1973, Antimitotic properties of withaferin-A and Ehrlich ascite tumor cells-cytological observations, Int. J. Cancer 5, 244), immunoactivation (B. Shohat, 1973, Antimittic properties of withaferin-A and Ehrlich ascite tumor cells-cytological observations, Int. J. Cancer 5, 244; M. Ziauddin et. al. 1996, Studies on the immunomodulatory effects of Ashwagandha, J. Ethanopharmacology, 50, 69–76), immunosuppression through inhibition of adjuvant arthritis and the graft versus host reaction (A. Fugner, 1973, Hemmung immunologisch bedingter entzundungen durch das pflanzensteroid withaferin A, Arzneim. Forsch 23, 932), cancer chemoprevention through selective inhibition of cycloxygenase-2 (B. Jayaprakasam and M. G. Nair, 2003, Cyclooxygenase-2 enzyme inhibitory withanolides from *Withania somnifera* leaves, Tetrahedron 59, 841–849), attenuation of tachyphylaxis to clonidine on electrically stimulated ileum in vitro (H. Matsuda et al., Structures of withanosides I, II, III, IV, V, Vi and VII, new withanolide glycosides, from roots of Indian *Withania somnifera* Dunal and inhibitory activity for tachyphylaxis to clonidine in isolated guinea-pig ileum, Bioorg. Med. Chem. 9, 1499–1507, 2001). It has also been suggested to be useful in cognitive dysfunctions and cause noortropic effects [J. N. Dhuley, 2001, Noortropic-like effect of Ashwagandha (*Withania somnifera*) in mice].

One of the most prolific producer plant, *Withania* (Ashwagandha in Hindi and Sanskrit, winter cherry in English) is the best source of withanolides particularly withaferin-A and has been recognized as a plant with multiple forms of medicine in Ayurveda, the most descript and extensive and one of the major Indian systems of traditional medicines. Currently, besides several forms of pure herbs and herbal extracts of *Withania* sold all over the world as herbal health helping GRAS (generally regarded as safe) products, Ashwagandha forms active ingredient of more than 100 Ayurvedic medicines, more than 30 Sidha medicines and a good number of Unani medicines.

It is well accepted that non-nutrient secondary metabolites form the basis of pharmacological value of these medicinal herbs. Thus, withanolidal phytochemicals like withaferin-A abundant and characteristic in *Withhania* and other producer plants are present day molecular medicinals avowal to the clinical significance of the plant and plant parts discerned in traditional medical practices. Thus, high yield isolation of withaferin A for various experimental, industrial and therapeutic utilities is of obvious importance. Furthermore, precision of dose of active ingredient is of fundamental and vital importance in any acceptable present day clinical practice. Accordingly, accurate estimation of its content, upto closest precision of its occurrence in planta or in materia is important to administer qualified dose(s) and ascertain/relate it to quantified effect(s). For these reasons, inter alia, quantitatively near to entirety of extraction are necessitated at both mass scale production and diagnostic analyses. In summation, efficient, effective and economical extraction/recovery of withaferin-A, as a process, is of tremendous importance to industrial, pharmacological, medicultural, analytical and allied clinical and agri-biotechnological and corporate interests.

Thus, this technological process invention draws its importance as relevance to one of the most critical requirement in the relevant withaferin-A based/centred trade and treatments whether as producer plant or plant part biomass or as products themfrom with the core concern of the quantitative isolation of withanolidal component of withaferin-A in the material of test and/or interest.

Although, some general protocols for post-harvest processing of plant materials of *Withania* species and other plants/plant parts containing withanolides have been adopted and described by a number of researchers interested in the digging out structural forms of the withanolidal molecules existing in the plant(s)/plant parts of interest from time to time. These methods teach most often than not harvesting of the material followed by shade drying of the material to fully de-aqueous state. The methods further teach that the dried materials be powdered and extracted with 100% methanol or 100% ethanol. However, these investigations have not attended the issue of differential extractability of specific withanolides in consonance with the considerations and cognizances of it being imposed by some structural traits, biogenetic and/or inter- and intracellular sequestration(s) etc. Even routine quantitative analyses carried out in the researches of the plant biological or biotechnological nature, have also been as such adopted from the protocols and processes of isolations taught by their chemical researchers counterparts, without assessing them in true analytical sense. To the best of our knowledge, there is no patent on any alternate or more effective or better in correctness or more precise in solvation and recovery of withaferin-A from holding materials nor any physical or biological state(s) etc. Alternative to dried material has ever been researched and requisitioned to invent a process for efficient isolation and accurately monitor quantitative abundance withaferin-A from the relevant plant materials and products therefrom. The methods for isolation of withaferin-A used so far have not been scrutinized to validate their efficiency as strictly defined relative concentrations/recoveries in numerical values. Accordingly, routinely for isolations and estimations of withaferin-A in the test plant or plant part or the tissue type obtained from the field or generated in vitro through culture techniques have been carried out by shade drying, powdering followed by extraction Soxhlet or sonication or microwave extraction in alcohol.

To the best of our knowledge, there is no patent advising a specific way of efficient isolation of withanolidal compounds from plant tissues for yields and/or quantitative diagnostics. In the U.S. Pat No. 6,153,198 Shibnath Ghosal advises that a *Withania somnifera* glycosides of withanolides (sitoindoisides) could be prepared by extracting root stock with an aqueous-alcoholic solvent (water-methanol or water-ethanol in 1:1 mixture i.e. 50% aqueous solution of alcohol.). The patent advises that this extract can be devoid of whatever withaferin-A that was co-extracted by further partitioning of the preparation with chloroform wherein chloroform preparation be discarded and chloroform insoluble part be processed for making the formulation with low levels of withanolides including withaferin-A.

Thus, the invented extraction process represents a case of exception to the foregoing fact pertaining to the quantitative extraction, recovery and quantitation of withanolides in the plant materials, extracts and preparations therefrom as they are actually present therein. Thus, extraction of withaferin-A in the literature so far has been quantitatively unevaluated to devise an extraction process that facilitates optimal quantitative recoveries and prevent under estimations due to sub-optimal extractions.

Furthermore, as a prior art only air or shade otherwise dried materials have been advised for isolating withaferin-A and then quantitating its amount in such an extract. This invention teaches the process of the fresh using fresh as well as dry plant materials to have full extractions. The use of fresh material avoids the degradative and/or metabolic transformation loss of withaferin-A during the course of such dessiccations. Such dessications may also accompany losses or recalcitrance to efficient extractions that lead to exacerbating errors in estimations and recoveries for quality control in biomass processing, manufacture, product formulation, cultivar evaluation and other diagnostics including those at the pharmacological and pharmacokinetic levels etc.

Besides attending the technical inaccuracies, as above in monitoring and yielding the withaferin-A from the resources when employing the routine methods taught by the published literature and other public domain documents, this invention saves several expenditures in the process for unit amount of withaferin A isolated.

Another concern not addressed by any disclosures in the open literature is the utility of processing fresh herbs for estimations in planta and other advantages associated with the process on account of that. These include better yields, estimations, saving time, space, and costs in drying, alteration in qualitative compositions, contaminations (environmental materials and inclusions particularly growth of microorganisms (molds, bacteria, fungi etc.) and insects and pests) and adverse effects due to them.

Thus, the industrial, economical and pharmacological, analytical and quality control related necessity of the process for economically extracting and estimating full quantitative amounts of withaferin-A from plant materials and products therefrom is quite obvious. This process has been invented in view of the still need for a process and procedure for isolating and purifying withaferin-A from appropriate biomass or material and medicaments in a commercially viable/valuable way for various established and other exploratory uses. Further, it is an analytically essentiallity that directly provides rightful recovery and evaluation of concentration of withaferin-A to from the basis of dose, does regimen and label claims of the products of commercial and pharmacological/clinical significance. Efficient extraction of herbs while preserving their medicinal values is a process art as well as biochemical science. Many extraction companies/groups/individuals might be delivering extracts of suboptimal potency or compositional description—knowingly or unknowingly either because of lack of their prior experimental evaluation extraction process(s) and other reasons.

While literature describes some methods through which withaferin-A has been advised to be isolated from a plant or plant part [e.g. Dinan L. et al., 2001, 'Chromatographic procedures for the isolation of plant steroids' Journal of Chromatography A 935, 105–123, (see pages 118 and 119) advise that withanolides be generally extracted from plant material with methanol or ethanol which should then be depigmented by routine partitioning following mixing with water. The aqueous methanol phase then should be partitioned against chloroform or dichloromethane or diethyl ether to extract out the withanolides. The method does not advise anything like extent of efficiency when applied to specific withanolide including withaferin-A. A. S. Veleiro et al. (2, 3-dihydrojabrosalactone-A, a withanolide from *Acnistus breviflorus*, Phytochemistry 24, 1799–1802, 1985) isolated some withanolides including withaferin-A from methanolic extract of the dry herb. In another report on radiotracer based biosynthetic studies these workers (biosynthesis of withanolides in *Acnistus breviflorus*: biogenetic relationships among the main withanolides, Phytochemistry 24, 2573–2575, 1985). Ahmed et al. 'Withanolides from *Physalis peruviana*; Phytochemistry 50, 647–651 (1999) have used 95% ethanol as the extractant to visualize the presence of some known and unknown withanolides in the air dried plant material.

G. Roja et al. ['Tissue cultures of *Withania somnifera*: Morphogenesis and withanolide synthesis' Phytotherapy Research 5, 185–187 (1991) have used 100% methanol to extract withanferin A from dried cultured shoots and tissues to quantitate its concentration. Similarly, M. Furmanowa et al. [In vitro propagation of *Withania somnifera* and isolation of withanolides with immunosuppressive activity, Planta Med. 67, 146–149, 2001] have extracted air-dried green parts of the in vitro raised plants in 100% methanol or ethanol for recovery of withanolides including withaferin-A.

Very recently (2003) B. Jayaprakasam and M. G. Nair (Cyclooxygenase-2 enzyme inhibitory withanolides from *Withania somnifera* leaves, Tetrahedron 59, 841–849) have extracted shade dried and ground leaves of *Withania somnifera* sequential with dichloromethane-methanol (1:1), 100% methanol and then water to theoretically scope for extraction under three widely discrete polarities to probably qualitatively have as many withanolides as possible including water soluble glyco-derivatives of withanolides. Thus, no specific extractant system has been designed and evaluated for recovery of withaferin-A or other withanolide. No extraction has been made under a system of narrow range polarity available with water-methanol admixture was attempted or evaluated for recovery in a withanolide specific manner. J. Zhao and associates (Withanolide derivatives from roots of *Withania somnifera* and their neurite outgrowth activities, Chem. Pharm. Bull. 50, 760–765, 2002) have adopted a routine method of isolating and recovering withanolides including withaferin-A from the *Withania* herb by extracting the root powder with 100% methanol. In the same way, H. Matsuda et al. used 100% methanolic extract of *Withania somnifera* dried roots to isolate withanolides (including withaferin-A) and withanosides (Structures of withanosides I, II, III, IV, V, Vi and VII, new withanolide glycosides, from roots of Indian *Withania somnifera* Dunal and inhibitory activity for tachyphylaxis to clonidine in isolated guinea-pig ileum, Bioorg. Med. Chem. 9, 1499–1507, 2001). S. Ray and S. Jha (Production of withaferin-A in shoot cultures of *Withania somnifera*, Planta Med. 67, 432–436, 2001) have quantitated concentration of withaferin-A in *Withania somnifera* shoot cultures produced under different compositions of in vitro culture medium after extracting the dried biomass in 100% alcohol (methanol).

Thus, all prior arts of researches for extraction of withaferin-A, none has attended the relative extractability of withaferin-A in different extractant compositions to arrive at the optimal system. For such an analysis, it is prerequisite to have a specific experiment designed and executed to have a range of extractions made with an admixture of water and appropriate alcohol and to have a comparison of recoveries under such conditions using dry and fresh tissue in quantitative terms to invent the most appropriate one for yields and/or estimation of concentrations. No attempts have been made to address this issue and concern.

The focused microwave-assisted extraction experiments of Kaufmann et al. ['Parameters affecting microwave-assisted extraction of withanolides' Phytochemical Analysis 12, 327–331 (2001)] on withaferin-A from air dried

*Iochroma gesnerioides* leaves, have assessed six variables viz. nature and volume of extracting solvent, sample moistening before extraction, extraction time, power of microwave irradiation and particle size. Their experiments concluded that for microwave extraction most favourable experiments were using powered material (as is usually done even in conventional extractions) previously moistened (600 microlitre per 100 mg dried material) helps improve microwave assisted extraction from the dry material to conceptually advise that the micro-waving in 100% methanol after moistening (as above) air dried leaves, helps in microwave-assisted methanol extraction (thus final extractant being about 95% methanol) of withanolides including withaferin-A because of better wave energy assimilation and promotion of cell disruption by internal superheating facilitating desorption of analytes from the matrix. The comparison has been made with conventional (soxhlet) extractions using 95% ethanol and 5% water. These workers, in another PSE instrumental extraction [Study of factors influencing pressurized solvent extraction, PSE, of polar steroids from plant material. ' Chromatographia 54, 394–398, 2001; 'Recent extraction techniques for natural products: microwave-assisted extraction and pressurized solvent extraction'. Phytochemical Analysis 13, 105–113, 2002) that a 1:1 mixture of methanol:water (i.e. 50% methanol) was useful in using pressurized solvent extraction (PSE) technology on air-dried leaf material. However, these revelations are related to operational parameters of the instrumental approaches of withanolide extractions rather than addressing the chemical characteristics/uniqueness of the molecules per se or in conjunction with their properties in biomass. Thus, serious concerns as how to appropriately extract withaferin-A in a solvent specific way as not been addressed nor the putative advantages of processing through the freshly harvested non-desiccated extractions, disjointed from the extraneous parameters of the instrumental mechanization or automation, has factually not been addressed.

Thus, it is clear that concerns like extractions from fresh herbs (for use in a variety of applications like resource authentication, quality assessment, metabolic, metabolomic and pathway analysis systems and devising post harvest technologies, avoiding drying times, space and money, man power and associated safety and contamination risks and hazards etc.) and use of suitably and stringently defined hydrated alcohol extraction with solvent/alcohol percentage narrowly gauged between 50% alcohol: 50% water to 100% alcohol: 0% water has not been worked out with respect to technological, diagnostic, productivity advantages in a withanolide specific way e.g. for withaferin-A. Additionally, it would offer wider ingenuousnesses e.g. in planta or in materia metabolome state for the withanolide. The approaches so devised have tremendous applications to boot accuracy of determinations and improved extractability with add on savings on several points at the bench level as well as at industrial scale in case of scale up strategies/systems, both in instrumentally unaided as well as mechanized/automate operation of the (agro)-chemical technology.

OBJECTS OF THE INVENTION

The main object of the present invention is to develop an improved process for analytical and quantitative isolation of withaferin-A from plant materials and products therefrom Another main object of the present invention is to develop a methodology for efficient and quantitative isolation and profiling of withaferin-A from the producer plants and products and formulations therefrom.

Yet another main object of the present invention is to develop extractant solvent compositions for high degree of extraction of withanferin-A from plants and other organisms and their products.

Yet another main object of the present invention is inclusion of stringently defined favourable proportion of water in the appropriate/compatible alcohol or other organic solvent in the extraction medium to achieve the better solvation of a withaferin-A present in the tissue and materials for metabolomics, metabolism, quality characterization and better yields in related analytical, pharmacological, nutritional industrial and research and auxiliary works.

Still another object of the present invention is to explore and employ appropriate state (fresh biomass or hydrated material) of the withanolide congener/holding materials.

Still another object of the present invention is to have the extraction medium still favouring for the recovery of more polar conjugates of withanolides (like glyco-derivatives etc.).

Still another object of the present invention is to develop a methodology to facilitate have the plant or material extract fully isolate/produce withaferin-A present therein from the same single extract that can be further fractionated in sequence or simultaneously in appropriate polarity solvent for yielding withanolides and their conjugates independently or together as per requirements of analyses and production.

Still another object of the present invention is to develop a process for accurate profiling of quantitative withaferin-A for standardization of relevant botanicals/herbal products/phytomedicines/nutraceuticals/food supplements in a more meaningful sense efficacy, safety and analogous concerns of producers, buyers, sellers, prescribers, pharmacists, practitioners, consumers etc. and for providing better label claims, certification for the development and definition of commercial products.

Still another object of the present invention is to put up the case of use of fresh biomass for preparation of phytochemical extracts of withanolides with respect to benchmarks or biomarks like withaferin-A from fresh herbs/biomass.

Still another object of the present invention is to use fresh or dry plant materials for withaferin-A preparation through translation of the extractant composition for its translation as technology process or agro (pharma)-technological operations in the trade irrespective of operational approach(s) of production like conventional instrumentally unaided or mechanized/automated.

Still another object of the present invention is to directly advantageously process fresh materials for withaferin-A preparation through translation of the extractant composition for its translation as technology process or agro (pharma)-technological operations and, thereby, minimize desiccation/air drying induced variability of withaferin-A contents/status.

Still another object of the present invention is to use fresh plant or plant materials for preparation of withanolidal extracts to avoid contamination of materials with microorganisms and environmental inclusions during drying without depleted yield of the phytochemicals and their concentration.

Still another object of the present invention is to use fresh plant or plant materials for preparation of withaferin-A extracts to save time, money, space and manpower on the activity of drying.

Still another object of the present invention is to use fresh plant or plant materials for preparation of withaferin-A extracts for its being adopted as a next on-farm activity as farmer's or grower's 'home-made phytochemical (HMP)' technology con-joint to agro-technology for withanolide producer medicinal/industrial plants.

Still another object of the present invention is to process fresh or dried plant or plant materials and products therefrom in lowering proportion of alcohol in the water: alcohol admixture of extractant without compromising on yields thus saving on solvent costs, invoking environmental benefits and minimizing personnel exposures and solvent ingrained contaminations e.g. as compared to full and nearly full (95%) alcohol.

Still another object of the present invention is to progress towards development of process fresh or dried plant or plant materials and products therefrom in the strictly and solvationally defined proportion of water in the water: alcohol admixture of extractants to select or devise or explore a single or mix of safe, cost effective, non-toxic, better acceptable, non-inflammable solvents of appropriate dielectric constant, dipole moment and polarity for better industrial or non-restrictive field applications in the withanolidal extract activities and enterprises.

Still another object of the present invention is to devise a process for optimal isolation of withaferin A from fresh or dried test plant or plant materials to develop better quantified and qualified chemotypes and mutants, with respect to withaferin-A and metabolomics of *Withania* and other producer/congener plants.

Still another object of the present invention is its utility and relevance in applying to the series of past publications and public domain data and other quantitative informations on withaferin-A, and put up it as IPR protected stantard operating protocol (SOP) it for future studies/monitoring/ evaluations etc. and along other relevant lines to re-address or re-tune, re-formulate the conclusions/products in qualitative and quantitative terms.

SUMMARY OF THE INVENTION

The present invention relates to a process for quantitative isolation of withaferin-A from plant materials and products therefrom, said method comprising steps of selecting the test material or plant or plant part or tissues, cells or organs of in vitro origin, extracting the material through routine methods either as dried or as fresh biomass in an extracting solvent system, with extraction solvent system consisting water: alcohol admixture with different proportions of water from 100% to 0%, defatting of the extract with usual partitioning with n-hexane followed by such chromatographic through a devised high-resolution analytical procedure of high performance liquid chromatography (HPLC) or through thin layer chromatography (TLC) system developed for most prolifically resolved profiling of withanlidal constituents including withaferin-A along the run track, after further portioning out the withanolidal aglycones including withaferin-A into chloroform followed by evaporating chloroform and dissolving the extract in known volume of methanol to have the 'extract for analysis', with quantification of the HPLC peaks using calibration curve of withaferin-A and also comparative visualization of intensities of specifically sparay reagent aided color-decorated spot of withaferin-A in TLC prepared after identical sample loading (i.e. the samples loaded in equal volume and were derived in the same weight to volume ratio of starting material versus volume of the 'extract for analysis' and run and developed under identical conditions amongst run on the same plate, and thereby making an assessment of the quantitative yield of withaferin-A in the material through the extracts so prepared and discerning the levels of extractivity of withaferin-A, in the fresh or dry plant material and assessing the extractability processes in terms of the relative efficiencies of solvent compositions of water and alcohol as above to discern the optimal one.

BRIEF DESCRIPTION OF THE ACCOMPANYING FIGURES/DRAWINGS

FIG. 1: TLC aided semi-qunatitative comparison of extraction and gross measure of Withaferin A under different extractant compostions

DETAILED DESCRIPTION OF THE INVENTION

Accordingly, the present invention relates to a process for analytical and quantitative isolation of withaferin-A from plant materials and products therefrom, said method comprising steps of selecting the test material or plant or part there or tissues, cells or organs of in vitro origin, extracting the material in an extraction solvent system, with extraction solvent system consisting of water: alcohol admixture with different proportions of water from 100% to 0%, defatting of the extract with usual partitioning with n-hexane followed by such chromatographic through high performance liquid chromatography (HPLC) (using our own high-resolution standardized procedure for withanolides) or through thin layer chromatography (TLC) system developed for most resolved profiling of withanlidal constituents including withaferin-A along the run track, after further portioning out the withanolidal aglycones including withaferin-A into chloroform followed by evaporating chloroform and dissolving the extract in known volume of methanol to have the 'extract for analysis', with quantification of the HPLC peaks using calibration curve of withaferin-A and also comparative visualization of intensities of specifically color-decorated spot of withaferin-A in TLC prepared after identical sample loading (i.e. the samples loaded in equal volume and were derived in the same weight to volume ratio of starting material versus volume of the 'extract for analysis' and run and developed under identical conditions amongst run on the same plate, and thereby making an assessment of the quantitative yield of withaferin A in the material through the extracts so prepared and discerning the levels of extractivity of withaferin-A, in the fresh or dry plant material and assessing the extractability processes in the terms of the relative efficiencies of solvent compositions of water and alcohol as above to discern the optimal one.

In an embodiment of the present invention is to develop a process for isolation of withaferin-A from plant materials and products therefrom.

In another embodiment of the present invention is to develop a methodology for efficient and quantitative isolation and profiling of withaferin-A from the producer plants and products and formulations therefrom.

In still another embodiment of this invention, the extractant solvent systems comprise specifically defined compositions of water:alcohol mixtures with proportion of alcohol within a narrow range around 60% to 80% (preferably 60% or accordingly 20 to 40% water in the alcohol:water admixture (preferably 40% water) for improved degree of extraction of withaferin-A from plants and other organisms and their products.

In still another embodiment of this invention, inclusion of substantial proportion of water (20 to 40%, preferably 40%) in the appropriate compatible alcohol (preferably methanol or ethanol) or other water miscible organic solvent of comparable polarity is key to have improved recovery or solvation of withaferin A from the matrix under the conventional or instrumentally aided isolation methods.

In still another embodiment of this invention, the stringently defined admixture of alcohol with substantial water proportion affords a favourable dielectric constant or dipole moment etc. or other chemical properties to the defined extractant (but nothing to do with or irrespective of its specific utility as facilitation of superheating and absorption of microwaves in the instrumental or automated or mechanized extraction) to facilitate achieve improved salvation of withaferin-A present in the tissue and materials for application in appropriate metabolomics, metabolic, quality characterization and better yields in related analytical, pharmacological, nutritional industrial and research and auxiliary works.

In still another embodiment of the present invention, the starting source tissue of withaferin A comprises preferably with fresh biomass for preparing extracts and providing the specific applications and several advantages without adverse impact in yields, quantitations etc.

In still another embodiment of the present invention, the designed specifically hydrated solvent system composition for withaferin-A is still suited for co-extraction of more polar withanolidal phytochemicals like glyco-conjugates, withanosides, sitoindosides, halo-withanolides etc.

Still another embodiment of the present invention, the process comprises of a methodology to enable the plant or material processing to better achieve/produce withaferin-A as well as other very closely related in structure or overall as metabolites that are much more similar withaferin-A and wherein enriched single extract that can be further fractionated in sequence or simultaneously in appropriate polarity solvent for yielding other withanolides (discriminative liquid:liquid partitioning for specific chemical entities within the chemical group of withanolides) and their conjugates independently or together as per requirements of analyses and production.

Still another embodiment of the present invention, the process provides means and ways of accurate quantitative profiling of withaferin levels for standardization of relevant botanicals/herbal products/phytomedicines/nutraceuticals/food supplements in a more meaningful sense of composition, efficacy, safety and analogous concerns of producers, buyers, sellers, prescribers, pharmacists, practitioners, consumers, better descript label claims etc.

Still another embodiment of the present invention, the process comprises use of fresh biomass for preparation of phytochemical extracts of withaferin-A from fresh herbs/biomass.

Still another embodiment of the present invention, the process provides methodology of using fresh plant materials for preparation of good withaferin-A rich extracts avoiding desiccation/air drying induced variability of withanolidal contents.

Still another embodiment of the present invention, the process uses fresh plant or plant materials for preparation of withaferin enriched extracts to avoid contamination of materials with microorganisms and environmental inclusions during drying without depleted yield of the phytochemicals and their concentration.

Still another embodiment of the present invention, the process comprises use of fresh plant or plant materials for preparation of withaferin-A rich or alternative withaferin-A depleted extracts for several advantages including phytochemical specific formulation, save time, money, space and man power on the activity of drying.

Still another embodiment of the present invention, the process comprises use of fresh plant or plant materials for preparation of withaferin-A extracts for its being adoption as a next on-farm activity as farmer's or grower's 'home-made phytochemical (HMP)' technology con-joint to agro-technology for withanolide producer medicinal/industrial plants.

Still another embodiment of the present invention, the process comprises steps to develop extractants like a single or mix of safe, cost effective, non-toxic, better acceptable, non-inflammable solvents of appropriate dielectric constant, dipole moment and polarity for better industrial or non-restrictive field applications in the withanolidal extract activities and enterprises.

Still another embodiment of the present invention, the process comprises a system and approach of better and optimal isolation of wihaferin-A from fresh or dried test plant or plant materials or herbal materials to develop better quantified and qualified chemotypes and mutants, with respect to withaferin-A and metabolomics of *Withania* and other producer plants, validated label claims of the products.

The following examples are given by way of illustration of the present invention and does not in any way limit the scope of the present invention:

EXAMPLES

Example 1

One gram of air-dried powdered leaf material from an identified plant of *Withania somnifera* (designated RS-1) was extracted three times with 20 ml each time of the liquid extractant in an Erlenmeyer flask by shaking on a platform shaker (10–30 RPM) for 8 hours in each extraction. Such extractions were carried out using different solvent compositions consisting of methanol: water proportions in the mixture being 0:100 (i.e. 100% water), 10:90 (i.e. 10% methanol in water), 25:75 (i.e. 25% methanol in water), 30:70 (i.e. 30% methanol in water), 50:50 (i.e. 50% methanol in water), 60:40 (i.e. 60% methanol in water), 75:25 (i.e. 75% methanol in water), 80:20 (i.e. 80% methanol in water), and 100:0 (i.e. 100% methanol). The extractions in the solvent composition were recovered by filtration and the filtrates from the three extractions in each case (of composition of extractant systems) were pooled and liquid-liquid partitioned (three times) with (equal volume) n-hexane to remove pigments and fatty materials. The defatted and depigmented extract was subjected to liquid-liquid partitioning (3 times, equal volume) to recover withanolidal fraction including withaferin A in the chloroform layer. Chloroform fractions of each extractant (solvent) systems were pooled and evaporated to dryness. The residue was dissolved in known volume (2.0 ml) of methanol and 5 µl was to subjected to high performance liquid chromatographic (HPLC) analysis using a standardized high-resolution binary gradient elution consisting of solvent A as water and solvent B as methanol each containing 0.1% acetic acid. The initial conditions were 65% A and 35% B changing to 30% A and 70% B in 45 min at a flow rate of 0.6 ml per minute, and then changing to 5% A and 95% B at 50 minute. The column was flashed for another 10 min with 100% B and then initial conditions were resptored for the next sample analysis. The analysis was performed on Binary Gradient System of M/S Waters consisting of two pumps, 996 photodiode array detector with Millenium Chromatography manager and 717 Autosampler. The column used was Nova Pak $C_{18}$ (150×3.9 mm, 4 µm) and detection-analysis was carried out at 227 nm. Calibration curves for withaferin-A was prepared for the sample (microgram) loaded (0 to 15 microliter of 1 mg per millilitre solution of withaferin-A in methanol) versus the peak area response in the HPLC chromatogram and the regressional analyse value (at 99% confidence) was used to quantitate withaferin-A from the HPLC chromatograms run under the identical conditions as reference. The results are tabulated below (Table 1).

TABLE 1

| Extractant Solvent-Composition [Methanol:Water] | Quantitative Recovery of withaferin-A in milligrams from one gram of powdered dry weight of *Withania somnifera* leaf (Percentage of maximal) |
|---|---|
| 00:100 | 2.43 (34.2) |
| 10:90 | 4.44 (62.4) |
| 25:75 | 5.90 (83.0) |
| 30:70 | 5.84 (82.1) |
| 50:50 | 6.44 (90.6) |
| 60:40 | 7.11 (100) |
| 75:25 | 4.87 (68.5) |
| 80:20 | 4.21 (59.2) |
| 100:100 | 1.49 (21.0) |

*Values in parantheses represent the percentage of the maximal quantity of withaferin-A isolated Evidently, about one third of withaferin-A is extractable aqueously. This affords a safer extractive approach for putting the products in the consumer chain. Secondly, it affords a cheaper way of extracting withaferin-A followed by its recapturing in non-polar solvent of choice like chloroform, ethyl acetate etc.

Further that the extraction in alcohol: water admixture in a proportion tightly tuned to proportions around 60:40 ratio are optimal for analytical and quantitative isolations. affording an improvement in recovery by about 4.8 fold over the 100% alcohol extraction. This is relevant to any aspect of concern like experimental, productivity, diagnostic etc. applied to biomass and/or products from them.

Example 2

Known weight (four mature leaves, about 4.0 gram) of freshly harvested leaf material from an identified plant of *Withania somnifera* (designated RS-1) was extracted three times with 20 ml each time of the liquid extractant in an Erlenmeyer flask by shaking on a platform shaker (10–30 RPM) for 8 hours in each extraction. Such extractions were carried out using different solvent compositions consisting of methanol: water proportions in the mixture being 10:90 (i.e. 10% methanol in water), 20:80 (i.e. 20% methanol in water), 25:75 (i.e. 25% methanol in water), 40:60 (i.e. 40% methanol in water), 50:50 (i.e. 50% methanol in water), 60:40 (i.e. 60% methanol in water), 75:25 (i.e. 75% methanol in water), 80:20 (i.e. 80% methanol in water), and 100:0 (i.e. 100% methanol). The extractions in the solvent composition were recovered by filtration and the filtrates from the three extractions in each case of composition of extractant systems were pooled and liquid-liquid partitioned (three times) with (equal volume) n-hexane to remove pigments and fatty materials. The defatted and depigmented extract was subjected to liquid-liquid partititoning (3 times, equal volume) to recover withanolidal fraction including withaferin-A in the chloroform layer. Chloroform fractions of each extractant (solvent) systems were pooled and evaporated to dryness. The residue was dissolved in known volume (1.2 to 1.5 ml) of methanol and subjected to high performance liquid chromatographic (HPLC) analysis as in example 1. The results are tabulated below (Table 1).

TABLE 2

| Extractant Solvent Composition [Methanol; Water] | Quantitative Recovery of withaferin-A in milligrams from one gram of fresh weight of *Withania somnifera* leaf (Percentage of maximal) | Data of fresh material extraction when expressed on corresponding dry weight basis (mg withferin A/g dry weight) |
|---|---|---|
| 10:90 | 0.58 (35.6) | 3.40 |
| 20:60 | 0.95 (58.3) | 5.60 |
| 25:75 | 1.01 (62.0) | 5.92 |
| 40:60 | 0.97 (59.5) | 5.71 |
| 50:50 | 1.26 (77.3) | 7.44 |
| 60:40 | 1.63 (100) | 9.60 |
| 75:25 | 1.60 (98.2) | 9.42 |
| 80:20 | 1.59 (97.5) | 9.37 |
| 100:00 | 0.83 (50.9) | 4.89 |

*Values in parentheses represent the percentage of the maximal quantity of withaferin A isolated Evidently, extractions from fresh biomass afford better range of consistency of extraction in quantitative terms. The extraction system composed of water:alcohol ratio of 40:60 to 20:80 (preferably 40:60) is optimal for the process for withaferin-A yields/recovery.

When expressed on per g dry weight basis, the recovery with 100% alcohol from fresh material afforded about 3.3 times improved yield of withaferin-A. With optimal composition devised herein (alcohol:water, 60:40), the yields with fresh material were 1.35 folds higher (35% improved).

Even 100% alcohol extraction of fresh biomass affords better extent (about 50% of maximal) of withaferin-A recovery compared to that with dry matter (about 20%, as shown in Table 1). Overall maximal yields with fresh material with their optimal extractants are better (about 35% improved, comparison of maximal values in column 2 of Table 1 and column 3 of Table 2).

Conventional full or even arbitrarily half aquated alcohol (50:50, alcohol:water) extraction are exacerbative to withaferin-A extraction for yield and underestimation for diagnostics and evaluations (of any kind) by about 50% and 33%, respectively). This is very important component invoking direct error of inappropriateness being 10–33% en bloc.

Thus, extractions in alcohol:water admixture in a proportion tightly tuned to proportions around 60:40 ratio are optimal to better recovery for any experimental, productivity, diagnostic etc. purposes applied to biomass and/or products from them.

Example 3

One g of the dry powdered leaf material was extracted with water (100%) thrice (20 ml each) by shaking for 8 h on platform shaker (10–30 RPM) and the three filtration-recovered aqueous extracts were processed as above in example 1 for liquid-liquid partitioning and estimation of withaferin A through HPLC. The residue after aqueous extraction was extracted three times with 100% methanol as above and processed for liquid-liquid partitioning and HPLC quantitation of withaferin A. parallel, 1.0 g of the powdered leaf extract from the same common stock of leaf powder of plant RS-1 was directly (without previous aqueous treatment and extraction) was subjected to withaferin A isolation and estimation as above in example 1. The quantitative observations on withaferin A recovery and tissue quantitation are given in Table 3.

TABLE 3

| Biomass | Extractant | Withaferin-A content in biomass (mg/g dry matter) | Quantitative value or yield of withaferin-A from one gram dry leaf powder (% of maximal) |
|---|---|---|---|
| (1a) One g dry leaf powder | 100% water | 2.43 | 2.43 + 3.26 = 5.69 mg (59.3%) |
| (1b) Residue from above extraction | 100% methanol | 3.26 | |
| (2) One g dry leaf powder | 100% methanol | 1.49 | 1.49 mg (15.5) |
| (3) One g dry leaf powder | 40% water in methanol | 7.11 | 7.11 mg (74.1%) |
| (4) Four g fresh leaf material (equivalent to 0.68 g dry matter | 40% water in methanol | 9.60 | 9.60 mg (100%) |

Evidently, (i) considerable amount of withaferin-A is extractable form the tissue or powder matrix in water, to the extent that the recovery is better than that with 100% alcohol (methanol) directly, (ii) pre-extraction or moistening of the material/matrix with water helps improve recovery in subsequent alcohol extraction significantly (3.26 mg per g matter as compared to 1.49 mg in methanol extraction as such, i.e. about two fold improvement. Nonetheless, the recovery is still sub-optimal (about 60%) compared to direct extraction of the dry or fresh biomass in water:alcohol mixture of 40:60. Furthermore, water assisted improvement in withaferin-A recovery is independent of approach of isolation (conventional or microwave or other instrumental aid) implying that it is strictly related to the solvation, chemical attributes, intracellular locale of it amassment or other intrinsic factors of the matter or withanolide rather than its usefulness in instrumental approach like augmentation of absorption of radiations like microwave, (iii) arbitrary extractions in alcohol or alcohol: water mixture accompany errors of underestimation or provide suboptimal withaferin-A, attribute wide variations in product qualities and infuse inconsistencies in product matching batch to batch, across pharmacies, (iii) the intricate profile of recoveries and the data herein imply that the patterns themselves provides guidelines to develop a range of quality products, (iv) to minimize biological variations in the phytochemicals like withaferin-A, extractants in the processes of analysis or manufacture should be stringently tuned to very narrow fluctuations around the alcohol:water ratio of 60:40.

Example 4

Known weight (four mature leaves, about 4.0 gram) of freshly harvested leaf material from an identified plant of Withania somnifera (designated RS-1) was extracted three times with 20 ml each time of the liquid extractant in an Erlenmeyer flask by shaking on a platform shaker (10–30 RPM) for 8 hours in each extraction. Such extractions were carried out using different solvent compositions consisting of methanol: water proportions in the mixture being 10:90 (i.e. 10% methanol in water), 20:80 (i.e. 20% methanol in water), 25:75 (i.e. 25% methanol in water), 40:60 (i.e. 40% methanol in water), 50:50 (i.e. 50% methanol in water), 60:40 (i.e. 60% methanol in water), 80:20 (i.e. 80% methanol in water), and 100:0 (i.e. 100% methanol). The extracts solvated in the solvent compositions were recovered by filtration, the filtrates from three extractions in each case of composition of extractant systems were pooled and liquid-liquid partitioned (three times) with (equal volume) n-hexane to remove pigments and fatty materials. The defatted and depigmented extract was subjected to liquid-liquid partititoning (3 times, equal volume) to recover withanolidal fraction including withaferin-A in the chloroform layer. Chloroform fractions of each extractant (solvent) systems were pooled and evaporated to dryness. The residue was dissolved in known volume (1.2 to 1.5 ml) of methanol and subjected to thin layer chromatography-aided semi-quantitative visual profiling in a comparative fashion. The TLC plate (pre-coated silica gel G, normal phase. E. Merck) high resolving solvent composition was discovered to be chloroform: ethyl acetate: methanol: benzene in a proportion of 70:4:8:24. The sample loaded (7.5 μl each) plates were developed by spraying anisaldehyde reagent followed by heating at 110 degree Celsius for 15 min. The results are presented in FIG. 1. The color density in the withaferin A spot gives a semi-quantitative comparison of the recoveries and estimations under the defined extractant compositions.

In FIG. 1, TLC aided semi-quantitative comparison of extraction and gross measure of withaferin A under the different extractant compositions. Lane 1, Standard (authentic) withaferin A; Lane 2, 10% methanol in water; Lane 3, 20% methanol in water; lane 4, 25% methanol in water; Lane 5, 40% methanol in water; Lane 6, 50% water in methanol; Lane 7, 60% methanol in water; Lane 8, 80% methanol in water; Lane 9, 100% methanol, lane 10, standard withaferin A. The density of pink spot gives a visual account of quantitative abundance of withaferin in the extract. Lanes 7 and 8 representing 60 and 80% methanol (preferably 60%) appear to be most extractive composition for withaferin A from fresh materials.

COMPARATIVE RECOVERY OF WITHAFERIN A FROM PRIOR ART

Example

Preparative Scale Isolation of Withaferin A from a Selected Plant of Withania Somnifera using the Method Invented Herein:

Withania somnifera leaves (1.5 Kg fresh weight, equivalent to 0.255 g dry weight) were extracted in methanol:water (60:40), extract washed upto removal of chlorophyll with hexane, hexane washed extract partitioned with chloroform and finally chloroform fraction dried and subjected to silica gel column chromatography using routine methods and eluting the column with solvent compositions of increasing polarity:hexane-ethyl acetate and ethyl acetate-methanol. Fractions predominantly containing withaferin A were pooled and withaferin A recovered by crystallization. Crystallized yield of withaferin A was 3.152 g.

Following is the comparative extent of gain in yield comparative to previous isolations reported in literature:

| Reference | Extraction Method | Recovery/ yield (g/Kg dry/ weight) |
|---|---|---|
| Abraham et al. Phytochemistry 14: 189–194, 1975 | Dried leaves (Israeli) extracted in ether and column chromatography | 2.375 |
| Kirson et al. Tetrahedron 26: 2209–2219, 1970 | Dried leaves (South African Plant) extracted in 100% methanol and column chromatography | 8.594 |

-continued

| Reference | Extraction Method | Recovery/yield (g/Kg dry/weight) |
|---|---|---|
| Kirson et al. J. Chem. Soc. © Org2032–2044, 1971 | Dried leaves (Indian Plant) extracted in 100% methanol and column chromatography | 1.667 |
| Anjeneyulyu and Satyanarayana Rao, Ind. J. Chem. 36: 1616–165, 1997 | Dried leaves (Indian Plant) extracted in 100% methanol and column chromatography | 0.333 |
| This invention | Fresh material leaves (Indian Plant) extracted in 60:40 (methanol:water) and column chromatography | 12.361 |

The Main Advantages of the Present Invention:
1. It provides a better process isolation of withanolides like withaferina from plant materials and products therefrom.
2. The process provides a methodology for efficient and more dependable quantitative isolation, estimation and profiling of withaferin-A from the producer plants and products and formulations therefrom.
3. The process enables better solvation of withaferin-A present in the tissue and materials which has edges of advantage and applications in research and development concerning metabolomics, metabolism, quality characterization and better yields in related analytical, pharmacological, nutritional industrial and research and auxiliary works.
4. It enables processing of fresh biomass for preparing withaferin-A which is useful and advantageous in several applications and operations of herbal industry without invoking adverse impact in yields, quantitations etc.
5. It also provides a means of simple discriminative liquid: liquid partitioning for getting extracts with enrichment of different withanolidal moieties.
6. The process also offers utilities in making preparations largely free from withaferin-A.
7. The process displays that even water extract offer as good (and safest too) means of withaferin-A recovery as alcohol.
8. The process displays that hydration of the dry matters or extraction of fresh materials is advantageous in analyses, manufacture processing and designing of Ashwagandha products.
9. The methodology enables the plant or material processing for better achieving/producing withaferin-A rich single extract that can be further fractionated in sequence or simultaneously in appropriate polarity solvent for yielding withanolides and their conjugates independently or together as per requirements of analyses and production.
10. The invention provides means and ways of accurate and real-state quantitative profiling of withaferin-A that is valuable for standardization of relevant botanicals/herbal products/phytomedicines/nutraceuticals/food supplements etc. in a more meaningful sense of composition, efficacy, safety and analogous concerns of producers, buyers, sellers, prescribers, pharmacists, practitioners, consumers, label claims etc.
11. The invented process facilitates use of fresh biomass for preparation of phytochemical extracts of withanolides from fresh herbs/biomass highly attractive parameter of advantage in relevant industrial operations.
12. The process provides methodology of using fresh plant materials for preparation of good quality-retained withaferin-A rich extracts with advantages of preventing desiccation/air drying induced variability of contents and compositions.
13. The invention provides advantages of using fresh plant or plant materials for preparation of withaferin-A extracts with respect to preventing contamination of materials with microorganisms and environmental impurities and inclusions during drying without depleted yield of the phytochemicals and their concentration.
14. The process provides economic benefits in terms of saving time, money, space and manpower on the activity of drying by facilitating uninhibited use of fresh plant or plant materials for preparation of withaferin-A extracts/products.
15. The process developed with respect to use of fresh plant or plant materials for preparation of withaferin-A extracts has the advantage of easily adopted as a next 'on-farm activity' to help farmer's or grower's and industries to practice 'home-made phytochemical (HMP)' technology con-joint to agro-technology for withanolide producer medicinal/industrial plants without any gestation time of drying. Thus, limiting providing gains over the drying operation associated disadvantages.
16. It has the advantage of being highly impetus to select or devise or synthesize a single or safe-mix, cost effective, non-toxic, better acceptable, non-inflammable solvent(s) of appropriate dielectric constant, dipole moment and polarity for better industrial or non-restrictive field applications in the withanolidal extract activities and enterprises.
17. The invention has the valuable utility of allowing undertaking of adopting a better system and approach of optimal isolation/yield of withaferin-A from fresh or dried test plant or plant materials to strengthen the reliability of developing or identifying quantified and qualified chemotypes and mutants of biogenetically active plants, with respect to withanolidal phytochemicals and metabolomics of *Withania* and other species.

It would be helpful in isolation and identifying newer withanolides particularly those less abundant in the tissues and/or escaped discernible recoveries so far in the highly alcoholized extractant used so far.

We claim:

1. An improved process for isolation of withaferin-A from plant materials, said process comprising the steps of:
    (i) extracting the plant materials in an aqueous alcohol extraction solvent,
    (ii) defatting the extract, as obtained in step (i), with partitioning with n-hexane followed by chromatographic separation to obtain a withanolide preparation,
    (iii) portioning out withanolide aglycones from the withanolide preparation, as obtained in step (ii), into chloroform followed by evaporation of said chloroform to obtain a chloroform extract, and
    (iv) dissolving the chloroform extract as obtained in step (iii) in methanol followed by chromatographic separation to obtain withaferin-A.

2. The process as claimed in claim 1, wherein the extraction solvent consists of water and alcohol in the ratio varying in the range of less than 100% to greater than 0%.

3. The process as claimed in claim 1, wherein the plant materials are selected from the group consisting of dry and fresh biomass of plant/plant material.

4. A process as claimed in claim 3, wherein the extraction is performed using a 60:40 methanol:water extraction solvent and the withaferin-A yield is about two fold greater than the withaferin-A yield obtained using a 100% alcohol extraction solvent and wherein the withaferin-A yield is about 30% greater than the withaferin-A yield obtained using a 50:50 methanol:water extraction solvent.

5. The process as claimed in claim 1, wherein the chromatographic separation technique is selected from group consisting of High Pressure Liquid Chromatography and Thin Layer Chromatography.

6. The process as claimed in claim 1, wherein the extraction solvent used is a mixture of water and alcohol.

7. A process as claimed in claim 1 or claim 5, wherein the chromatographic separation is done using Thin Layer Chromatography (TLC) with a high resolution TLC system for withanolides including withaferin-A comprising a plate running solvent composition of chloroform:ethyl acetate:methanol:benzene in the proportion of 70:4:8:24.

8. The process as claimed in claim 1, wherein the percentage of water in the extraction solvent system is in the range of 20% to 40% and rest is alcohol.

9. The process as claimed in claim 1, wherein percentage of water in the extraction solvent is 40% and rest is alcohol.

10. A process as claimed in claim 2 or claim 4, further comprising selecting an alcoholic solvent for use in the extract solvent, the alcoholic solvent being selected from the group consisting of a water-miscible group comprising at least one of methanol, ethanol and another alcohol with compatible polarity, dielectric constant and dipole moment or any single solvent devised to have such chemical properties.

11. The process as claimed in claim 2 or claim 4, wherein the extraction solvent is used to co-extract polar withanolide phytochemicals selected from the group consisting of glycoconjugates, withanosides, sitoindosides and halo-withanolides.

12. A process as claimed in claim 1, wherein products from said plant materials are in a form selected from the group consisting of a powder, a paste, sap, a capsule, a tablet, and a syrup.

13. A process as claimed in claim 1, wherein extraction of withaferin A is from fresh herbs and provides a withaferin-A yield that is greater than the withaferin-A yield obtained from dried herbs and is accurate in planta estimations in the solvent compositions developed for withaferin-A.

14. A process as claimed in claim 5, wherein the chromatographic separation technique used is High Pressure Liquid Chromatography (HPLC) and the separation is performed using a high resolution HPLC system for withanolides including withaferin-A comprising of a reverse-phase column run with a gradient mobile phase comprising a solvent A (methanol) and a solvent B (water) each solvent comprising 0.1% acetic acid, wherein the chromatographic separation begins with 65% A and 35% B and linearly changes to 30% A and 70% B in 45 minutes and then reaches 5% A and 95% B 5 minutes later.

* * * * *